United States Patent [19]

McFarlane

[11] 4,404,159

[45] Sep. 13, 1983

[54] APPARATUS AND PROCESS FOR FORMING A TAPERED TIP END ON A PLASTIC TUBE

[76] Inventor: Richard H. McFarlane, 2571 Kaneville Rd., Geneva, Ill. 60134

[21] Appl. No.: 243,899

[22] Filed: Mar. 16, 1981

[51] Int. Cl.³ .............................................. B29C 24/00
[52] U.S. Cl. .................................... 264/296; 264/322; 425/393
[58] Field of Search ...................... 264/322; 425/324.1, 425/393

[56] References Cited

U.S. PATENT DOCUMENTS

| 213,581 | 3/1879 | Mattson | 264/322 |
|---|---|---|---|
| 219,218 | 9/1879 | Carpenter | 264/322 |
| 2,296,296 | 9/1942 | Shaw | 264/334 |
| 2,900,665 | 8/1959 | Walker | 264/322 |
| 2,958,898 | 11/1960 | Voumaud et al. | 264/322 |
| 3,983,203 | 9/1976 | Corbett | 264/322 |
| 4,126,291 | 11/1978 | Gilbert et al. | 425/556 |
| 4,256,449 | 3/1981 | Sauer | 425/324.1 |

Primary Examiner—Jay H. Woo
Attorney, Agent, or Firm—John Cyril Malloy

[57] ABSTRACT

An apparatus and process for forming a feathered tapered tip on a plastic tube which utilizes a mandrel mounted relative to a work table to slidably receive and support a catheter in an aligned relation to the forming aperture in a tip forming die assembly, normally disposed in a spaced apart relation to the tube tip end. The die assembly preferably includes two portions, a first portion to slidably receive and support the tip end therethrough and to direct it into a tapered forming cavity in a second die portion. The first die portion is cooled and the second die portion is electrically heated, and the two portions, normally disposed in a spaced apart relation, are, first, cam operated into engagement and, second, are cam operated onto the catheter tip end, whereupon the tip end is tapered in response to the heat generated in the second die portion. The die portions are then cam operated out of engagement with the tip end and out of engagement with each other, and the catheter is removed from the mandrel.

26 Claims, 11 Drawing Figures

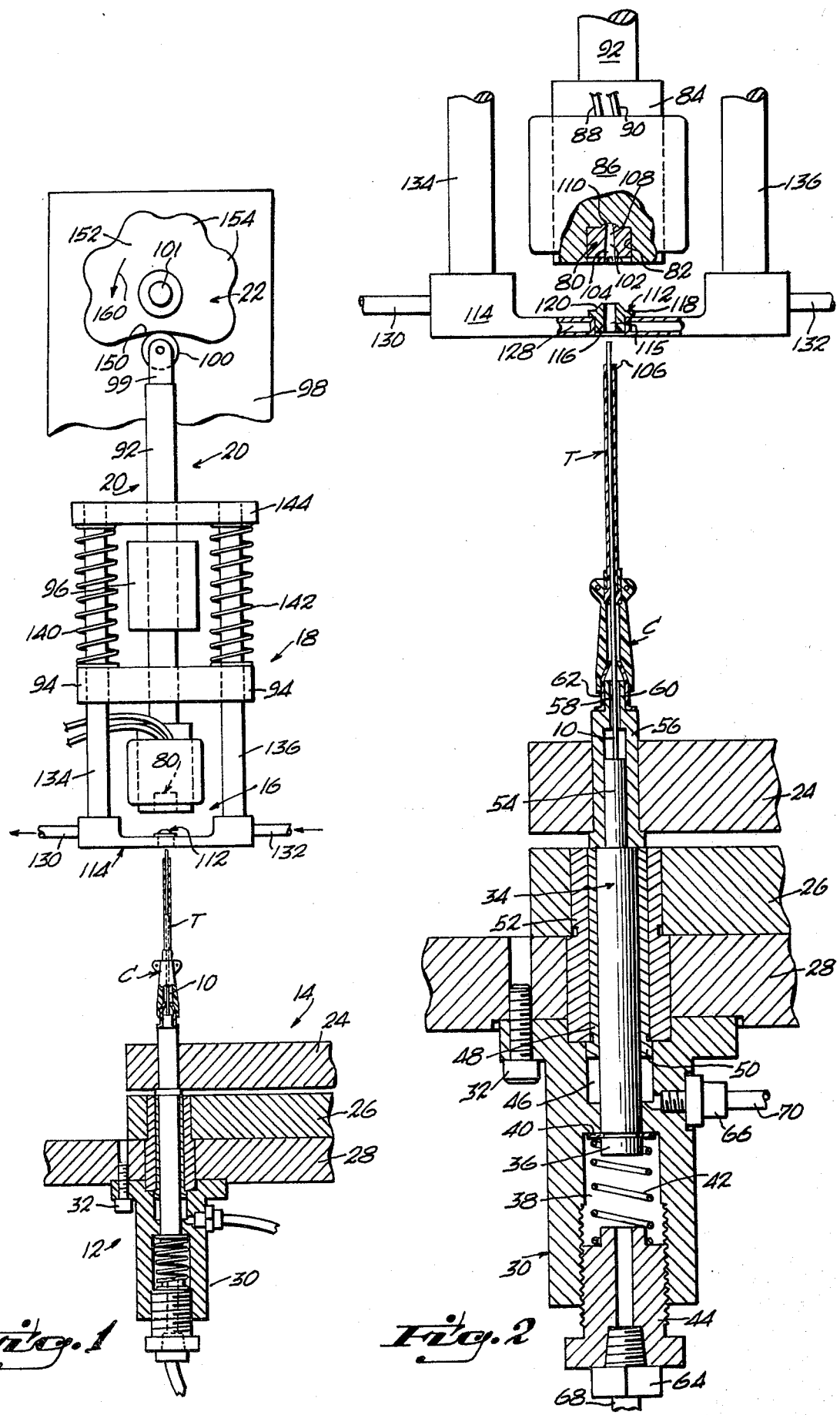

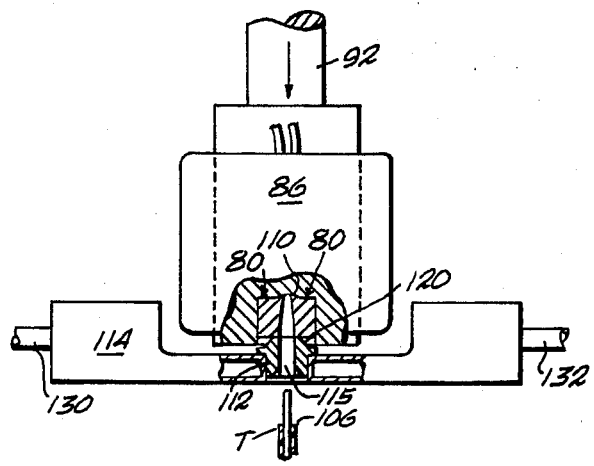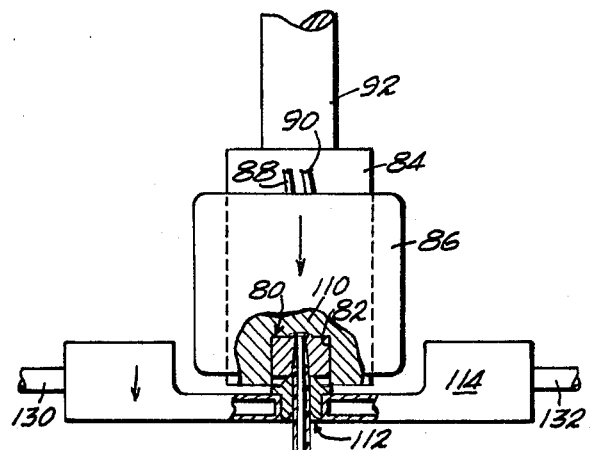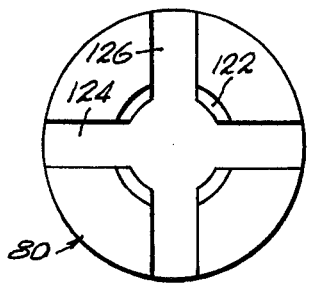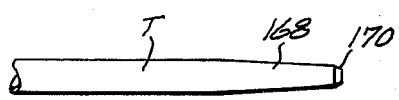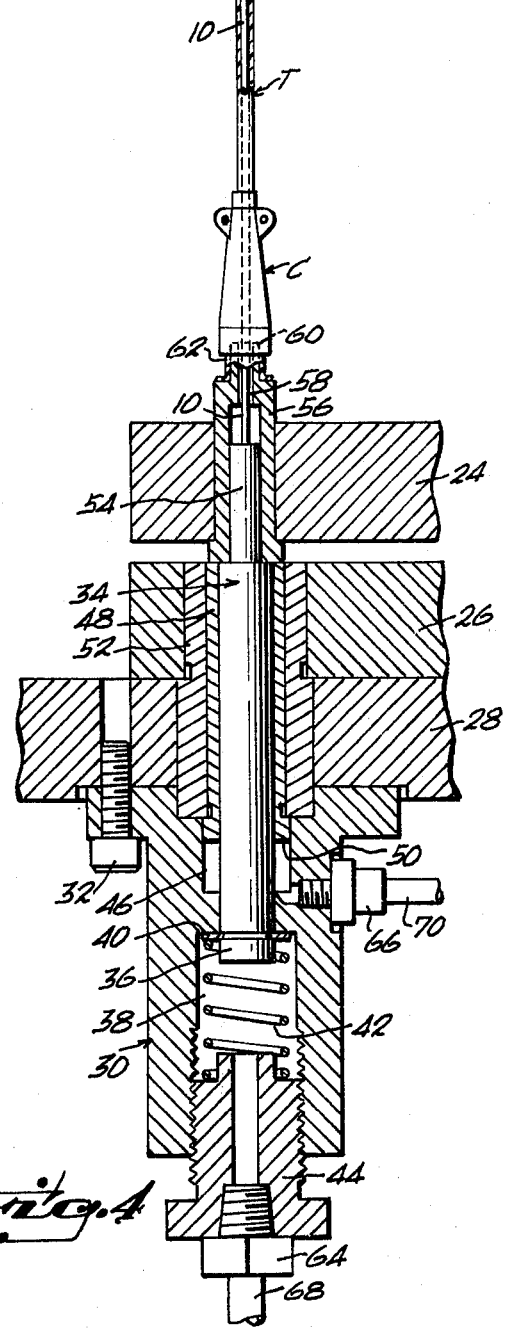

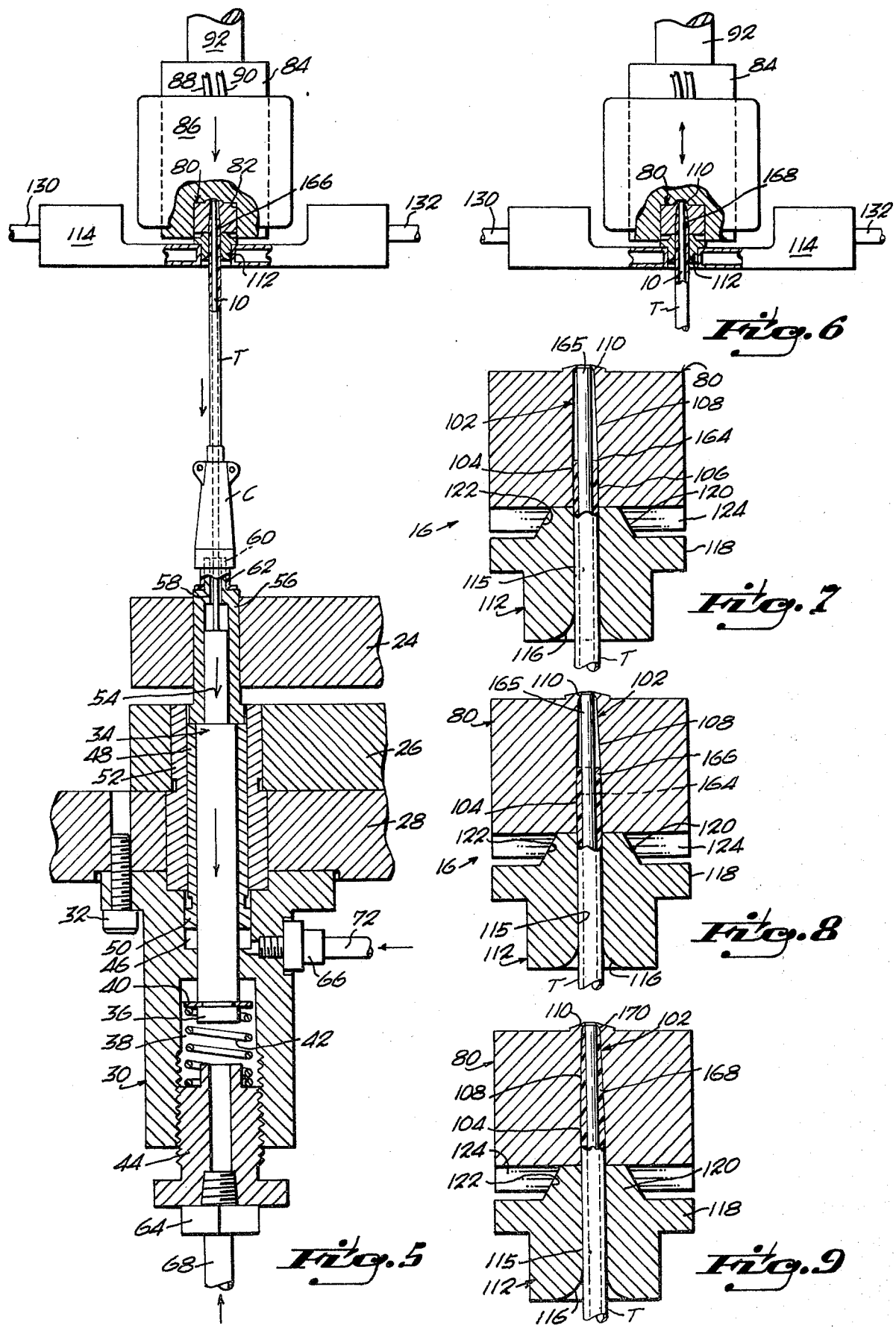

APPARATUS AND PROCESS FOR FORMING A TAPERED TIP END ON A PLASTIC TUBE

BACKGROUND OF THE INVENTION

It is quite often desirable to provide a feathered tip or feathered distal end zone on a relatively thin walled tube, such as a flexible catheter for injecting fluids intravenously into a patient. Such a tip should be smooth and gradually tapered. In the past this has been a difficult structure to produce. In the prior art it is known to grind the ends of plastic tube lengths to provide a taper or cut a taper on the end of such tubes. Because the same are thin walled this is a difficult, time-consuming and relatively expensive process. This invention is of an apparatus and process for forming a feathered tip on a plastic tube rendering it suitable for use as a medical catheter. It is also important that a plastic tube length, not only have a feathered tip but that the feathered tip closely conforms to a needle extending through and from the feathered end of the catheter so that when the needle jacketed by the catheter is inserted, flesh particles do not become trapped in the gap between the needle and the feathered catheter tip restricting movement of the catheter along with the needle to a point of positionment within a vein so that the needle can be withdrawn and the flow take place through the flexible relatively soft catheter. Also in the prior art, although it is known by various means other than that disclosed herein to taper the tips of such catheters for the purpose mentioned above, there is an additional problem. If the taper proceeds axially to a very thin feathered end, the end zone is relatively weak and hence susceptible to damage during insertion. Hence, it is preferred to provide a taper of the catheter tip zone in two stages, a proximal stage of tapering and a rather abrupt distal end zone taper so that the axial length of the thinnest portion is relatively short at the distal end. Finally, there is an additional problem and that is that after a tip has been processed according to prior art techniques it is important that the diameter of the tip zone be sized so as to snugly fit the needle so that a smooth insertion can take place of a needle jacketed by a catheter. It is believed that in the prior art it has been known to insert the end of a previously tapered tube into a heated die in an effort to form it by reducing the diameter to a proper configuration to mate with a needle to be used with it.

Further, it is believed that some in the prior art heat a die while engagedly the tip is being formed and retain it in engagement until the tube, tube tip and the forming die has been cooled by some type of cooling means.

The present invention is of an apparatus to rapidly and inexpensively make catheters with feathered tips as is described more fully hereinafter.

SUMMARY OF THE INVENTION

It has been found that when a tube to be feathered at a tip is formed by a die, such as a Teflon tube, which is the material preferred in this invention, heat must be applied to the tip to taper it with the die having a generally conical recess. When the heat is applied that portion of the tube adjacent the die tends to deform and wrinkle on the exterior and the interior surface rendering it unsuitable for insertion into the skin and a vein of a patient. This invention is of a die in two portions to be moved over a mandrel jacketed by a tube to be tipped wherein the portion of the die which moves axially furtherest over the tip is cooled or cooler relative to another portion of the die at the tip zone being formed so that wrinkling does not occur with the cooled die portion circumferentially supporting the tube while it is being formed by the heated or hotter portion of the die, which is quite difficult to do because the die being metal has high heat exchange or heat conductive qualities. Hence, one object of this invention is to provide a die in two portions, one portion comprising a generally cylindrical portion which includes a heat sink or cooling means and another portion which is tapered generally conically which is heated to feather the tip at the distal end of the tube.

It is another object of this invention to provide a die which is preferably in two pieces which are maintained in spaced axial relation from one another when not in use forming a tip and which are in abutting engagement with one another while the tip forming process is taking place and wherein a cooling means, such as a water cooling jacket is provided for the portion of the die about the cylindrical zone adjacent the feathered end of the tube and the heated portion does not transfer all of the heat required to form the tip but, rather, a temperature gradient is maintained between the two pieces so that the cooled portion is at all times at a lower temperature than the heated portion.

It is another object of this invention to provide a cyclical pulsing of the die during the forming process so that there is a reciprocal axial movement so that heat exchange between the heated portion and the tubing formed, preferably of Teflon, at the feathered tip permits an intermediate application of heat and the heat transfer time required is altered or adjusted as the heat is applied and air may be released between the mandrel on which the tube is positioned and the die and it can escape from between the mandrel, die and tube tip being formed.

It is another object of this invention to provide a means for yieldingly supporting the tube for relative axial movement of adjustment as axial forces are applied by the die to the tube tip.

It is a further object of this invention to provide a second biasing means for the mandrel about which a tube is positioned so that during the tip forming process the mandrel is able to move axially in movements of adjustment relative to the tube being formed so that movements of adjustment in response to axial forces applied by the die can yieldingly in a cushioned fashion take place.

In accordance with these and other objects which will become apparent hereinafter, the instant invention will now be described with reference to the accompanying drawings in which:

DESCRIPTION OF THE DRAWINGS

FIG. 1 is a front plan view, partially in cross section, of a device for forming a tapered end on a plastic tube;

FIG. 2 is an enlarged view, similar to the lower portion of FIG. 1, illustrating a first step in the process of forming a tapered tip end on a plastic tube;

FIG. 3 is a view similar to the upper forming die means of FIG. 1, illustrating a second step in the process;

FIGS. 4 and 5 are views similar to FIG. 2, illustrating subsequent steps in the process;

FIG. 6 is a view similar to FIG. 3, illustrating a final step in the tip end forming process;

FIGS. 7, 8 and 9 are substantially enlarged cross sectional views of the tip forming die members as disclosed generally in FIGS. 4, 5 and 6;

FIG. 10 is a bottom plan view of the upper tip forming die of FIGS. 7, 8 and 9; and FIG. 11 is a fragmentary plan view of the tapered tip end of a plastic tube in accordance with the present invention.

DESCRIPTION OF THE PREFERRED EMBODIMENT

In the preferred embodiment, the diameter of the mandrel is between 0.020 and 0.060 inches with the catheter lengths usually being between ¾ inches and up to 18 inches if desired. The diameter of the tube is such as to closely jacket or snugly jacket the mandrel and provide a relatively easy slide fit for positioning of the tube. The wall thickness of the Teflon tubes in the preferred use of the invention is between 0.005 and 0.010 inches.

The taper at the tip is about 0.002 inches in thickness to the knife edge at the very distal most end, where in the preferred embodiment it converges at an angle of about 30 degrees to the mandrel whereas the main tapered length is about 2 degrees of taper. Generally speaking Teflon softens at about 500° F.; and the heat of the heated portion of the die is such as to cause a softening of the Teflon, that is, preferably at a temperature between 500° F. and 600° F. Excessive heats, that is, heats substantially above 700° F. are not utilized. This is to avoid a rapid heat exchange to the mandrel itself at the seat. If allowed such excessive temperatures would, by conduction, cause the length of the mandrel to become heated rapidly, thereby causing wrinkling or buckling beyond the cooled support portion of the die which surrounds the tube. In a preferred operation, it will be appreciated that the application of the heat may take place in stages, such as at a three stage location where the heat is applied in three successive phases of operation of heat application depending upon the amount of forming to be done at the tip. For example, a turn table operation with three separate applications of the die may be utilized to complete the forming of a tube configuration at the tip.

Referring to the drawings wherein like reference characters designate like or corresponding parts throughout the several views, FIG. 1 is a general view, partially in cross section, illustrating a catheter C mounted on a mandrel 10 of a mandrel operating assembly 12, fixed relative to a work table assembly 14. A die assembly 16 is disposed above the mounted catheter C in a carriage assembly 18, the die assembly 16 being operably connected at 20 to an operator cam 22.

With particular reference to the work table assembly 14, FIGS. 1, 2, 4 and 5, three generally horizontal plates are illustrated, a top plate 24, intermediate plate 26 and a bottom plate 28. A housing 30 is bolted at 32 beneath the bottom plate 28 and a vertically operating piston 34 includes a lower end portion 36 disposed within an interior chamber 38 of housing 30. A stop ring 40 is fixed relative to piston 34 within lower chamber 38 to provide axial engagement with a compression spring 42 disposed in chamber 38 between said ring 40 and a screw plug 44 engaged through the bottom of housing 30, and limit upward movement thereof in response to the compression spring 42.

An upper chamber 46 is defined in an upper portion of housing 30 and a lower piston sleeve 48 disposed about piston 34 includes an enlarged headed lower end 50, slidably engaged in upper chamber 46. Piston sleeve 48 is slidably engaged in a sleeve bearing 52, fixed through the intermediate and bottom plates 26 and 28, and an upper piston sleeve 56 disposed about an upper reduced diameter piston portion 54 of piston 34 is slidably engaged through the top plate 24.

The mandrel 10 is fixed relative to upper piston portion 54 and extends axially outwardly therefrom through a hole 58 in a top end of the upper piston sleeve 56. Said piston sleeve 56 includes a top end nipple 60 and defines a seat for the conventional cupped outer end 62 of a catheter C.

Respective fittings 64, 66 connect a pair of tubes 68, 70, from a suitable compressed air source (not shown), to lower chamber 38 and upper chamber 46 for a purpose to be subsequently described.

With particular reference to the die assembly 16, it includes an upper tip end forming die member 80 fixed within a cavity 82 in a lower end of a block 84 formed of a suitable heat conductive material, and electric heater means 86 fixed about block 84 and connecting to a suitable electric source by leads 88, 90. Block 84 is fixed to a lower end of a slide rod 92 journaled through a pair of lower and upper blocks 94, 96, fixed to an upright member 98, fragmentarily illustrated. A cam follower roller 100, rotatably supported in a yoke member 99, fixed to an upper end of rod 92, is engaged against the operator cam 22 by conventional tension means such as a spring (not shown). Cam 22 is fixed to a shaft 101 which is power operated in any conventional manner such as by an electric motor (not shown).

As illustrated in FIGS. 2 through 9, the tip forming die member 80 includes an axially extending through cavity 102 including a minor cylindrical lower portion 104 of a diameter to receive the normally straight tip end 106 of a catheter tube T. The major upper portion 108 of cavity 102 is gently tapered to an upper terminal end portion which is provided with a substantially increased degree of taper at 110.

A lower portion 112 of the die assembly 16 is fixed through a heat sink or coolant receptacle 114 and includes an axially extending through aperture 115, cylindrically sized to receive the tube T therethrough and including a rounded bottom lead in entrance opening 116. The top side of die portion 112 includes an annular flange 118 and an upwardly, inwardly tapered central extension 120 for nested engagement within a mating, tapered recess 122 in the bottom face of die member 80, as best seen in FIGS. 7, 8, 9 and 10. As best illustrated in FIG. 10, preferably the bottom face of die portion 112 includes a plurality of radially disposed slots 124, 126 for reducing heat exchange contact between portions 80 and 112.

The coolant receptacle 114 defines an inner chamber 128 for reception of a suitable coolant, such as water, and is provided with respective inlet and outlet conduits 130, 132. A pair of slide rods 134, 136, vertically fixed relative to respective sides of receptacle 114 are slidably engaged through lower block 94 and fixed at upper ends to a tie bar 144. A pair of compression springs 140, 142 are disposed about respective rods 134, 136 between fixed block 94 and the tie bar 144.

Cam 22 is illustrated in a neutral position with a dwell portion 150 thereof in engagement with the follower roller 100. The major operating portion 152 of cam 22, preferably includes a plurality of lobes 154 for a purpose to be described relative to the operation of the device.

In practice, the above described apparatus may be duplicated at a plurality of stations about an indexing table, however, the drawings and above description relates to a single device and the process of taper forming the tip end of a catheter tube on a mandrel. However, it is to be understood that pluralities of loading, forming and unloading stations may be provided for production purposes.

In the illustration of FIGS. 1 and 2, a catheter C is inserted over the mandrel 10 and seated over the nipple 60 on the piston sleeve 56 and the table assembly 14, as illustrated, is indexed to axially align the catheter tube T with the aperture 115 and cavity 102 of the die members 112 and 80. The die member 80 is heated by the heater 86 and block 84, and a coolant is circulated through the receptacle 114 to maintain the die member 112 in a relatively cool condition.

As the cam begins its rotation, indicated by arrow 160, the heater 86 and die block 84 are driven downwardly, FIG. 3, to seat the tapered extension 120 of die member 112 in the bottom recess 122 of die member 80.

Further movement of cam 22 drives the coolant receptacle 114 with die member 112 downwardly, FIGS. 4 and 7, against the forces of springs 140, 142 until the normally straight cylindrical tip end 106 of Tube T passes through aperture 115 of die member 112 and engages the wall bend 164, FIG. 7, at the bottom end of the taper portion 108 of cavity 102. It is to be noted that a tip end portion 165 of mandrel 10 normally projects beyond the tip end of catheter C to seat against the increased taper portion 110, closely adjacent to the inner periphery thereof.

Further movement of cam 22 drives the piston 34, 54 downwardly against the forces of spring 42 and compressed air in chamber 38 from conduit 68, and forces the end portion 165 of mandrel 10 securely against the taper portion 110 to provide an effective seal for the top end of the taper portion 108 of cavity 102. Simultaneously, the catheter C depresses the piston sleeves 48, 56 by means of the contact of the tip end 106 of tube T with wall bend 164.

At this point the heated die member 80 is softening the tip end 106 and compressed air in chamber 46 from conduit 70 forces the piston sleeves 48, 56 and catheter C upwardly and the tip end 106 of tube T begins to taper within the cavity portion 108, as at 166, FIG. 8. FIGS. 6 and 9 illustrate the final phase of the forming operation in which the tapered end 168 of tube T is completed with an increased taper 170 at the very tip end as defined by the cavity terminal end 110.

The plurality of lobes 154 on cam 22 serve to jog the dies 80, 112 during the forming operation to relieve the air pressure build-up which would normally occur within the cavity portion 108.

While the instant invention has been shown and described herein in what is conceived to be the most practical and preferred embodiment, it is recognized that departures may be made therefrom within the scope of the invention, which is therefore not to be limited to the details disclosed herein but is to accorded the full scope of the claims so as to embrace any and all equivalent apparatus and processes.

What is claimed is:

1. An apparatus for forming an open ended feathered tapered tip on a thin-walled plastic tube, said apparatus comprising:
a die assembly structured and configured to receive and shape the tip of said plastic tube, a mandrel fixedly attached in supported relation to a movably mounted piston means, a support means structured for fixed positioning of said tube relative to said movable die assembly and movable mandrel, said mandrel disposed in aligned relation to said die assembly and structured to at least partially support said plastic tube thereon in slidable relation thereto; said die assembly comprising a heated die portion and a cooled die portion; activating means connecting to both said heated and cooled die portions and structured to dispose said die portions into and out of operative forming relation to said tube tip and in surrounding relation to said mandrel; said heated die portion including a cavity comprising a lower portion and an upper portion disposed in contiguous relation to one another, said upper portion having a tapered configuration and resultant decreasing diameter from its junction with said lower portion to a terminal end of said cavity, said terminal end defining a seat for engagement with the distal end of said mandrel protruding from said tube tip being formed, said mandrel and supporting piston movable relative to the substantially fixed position of said tube along with said die assembly, said tube tip being heated and forced into said upper portion of said cavity, whereby said tube tip is formed into an open ended feathered tapered configuration in conformance with the configuration of said cavity.

2. An apparatus as in claim 1 wherein said cooling die is movably disposed in spaced apart relation to said upper portion and forced into adjacent position relative to said heated die portion upon activation of said die assembly and movement of said heated die portion into surrounding telescoping relation over said mandrel and supported tube tip.

3. An apparatus as in claim 2 wherein said cooling die comprises a heat sink and is positionable in surrounding telescoping relation to said mandrel and supported tube immediately adjacent to said heated die portion, whereby said tube portion immediately protruding from said cavity has excessive heat removed therefrom.

4. An apparatus as in claim 3 wherein said heat sink comprises a cooling means in the form of a liquid cooled jacket surrounding said cooled die portion.

5. An apparatus as in claim 1 wherein said activating means includes means to cyclically and joggingly move said die assembly when in telescoping relation over said mandrel and said tube, whereby trapped air is released between the die, mandrel and softened flowable plastic and to permit heat transfer intervals of the heat from the heated die portion to the plastic.

6. An apparatus as in claim 5 wherein said activation means comprises a cam follower and a cam surface including a plurality of lobes, said cam follower mounted on a slide rod secured to said die assembly for operative positioning thereof.

7. An apparatus as in claim 1 wherein said piston means and attached mandrel is slidably mounted relative to said support means, said piston means comprising a housing secured in cooperative relation to one end of said piston means opposite said mandrel, biasing means disposed in biasing relation to said piston means adjacent said one end and being structured to bias said piston means and attached mandrel outwardly towards said die assembly.

8. An apparatus as in claim 7 wherein said biasing means comprises a fluid chamber disposed in said housing and spring means both disposed in cooperative relation to said one end of said piston means, said piston means and attached mandrel forced against the normal biasing force of said biasing means and said mandrel movable relative to said fixed position of said tube upon engagement of said distal end of said mandrel with said mandrel seat and activation of said die assembly into tube tip forming position.

9. An apparatus as in claim 1 wherein said heated die portion and said cooled die portion each include cooperatively positioned attaching structure configured to provide mating, substantially nesting engagement therebetween upon abutting engagement of said heated die portion with said cooled die portion and operation of said activating means.

10. An apparatus as in claim 2 wherein said cooled die portion comprises a through aperture disposed in aligned relation to said cavity of said heated die portion and dimensioned and configured for surrounding disposition relative to said mandrel mounted tube and in heat transferring relation thereto, whereby excess heat is removed from the surrounding portion of said tube.

11. A process for forming a tapered tipe end on a plastic tube providing an open passageway therethrough, the process comprising:
providing a mandrel of predetermined length resiliently mounted in a support means, and including a nipple formed atop said resilient mounting, to supportingly engage a first open end of the passageway of said mandrel extending a predetermined distance outwardly of a tip end at a second end of the passageway of the tube;
providing a heated die means, normally supported in a predetermined spaced position outwardly of said tip end and including an interior through cavity of a predetermined size and tapered configuration in axial alignment with said tip end;
providing a cooled die means and normally supporting said cooled die means in spaced relation from said heated die means and said tip;
providing actuating means to move said heated die means into mating engagement with said cooled die means and subsequently into heating engagement with said tip end and cooling engagement with said next adjacent tube portion to said tip and movably depressing said resilient mounting relative to said tube a predetermined distance inwardly, returning said resilient mounting to initial start position as a tip end portion of the plastic tube is heated and softened by said heated die means and enter said interior through cavity, to form a tapered end on said tube, conforming with said size and tapered configuration of said heated die means through cavity.

12. A process as in claim 11 including carrying said cooled die means in a resiliently mounted container containing a cooling agent, in a normally spaced position between said heated die means and tip end, said cooled die means including a through aperture sized and configured to receive the tubular member therethrough, said aperture being in alignment with said through cavity and tip end, said actuating means, first, operates said heated die means into engagement with a top side of said cooled die means and, second, moves said heated die means and cooled means into a position of through penetration of said aperture by said tip end portion, with said tip end in engagement with said heated die means through cavity for entry thereinto.

13. A process as in claim 12 wherein entry and exit means are provided in said receptacle to provide a flow-through stream of said cooling agent.

14. The process as defined in claim 12 wherein said cooled die means includes a central upwardly projecting tapered projection for seated engagement within a companionately sized configurated recess in a bottom wall of said heated die means.

15. The process as defined in claim 14 including radially extending slot means, extending outwardly through said heated die means bottom wall, from said bottom wall recess.

16. The process as defined in claim 11 wherein said heated die means comprises a die member disposed in a block of a heat conductive material, surrounded by an electric heater device.

17. The process as defined in claim 16 wherein said actuating means commmprises an appropriately configurated driven cam engaged with a cam follower carried on a first rod end, a second end of said rod being fixed relative to said block to transmit movements, imparted to said follower by said cam, to said heated die means.

18. The process as defined in claim 11 wherein said resilient mounting comprises a piston assembly slidably mounted in a work table, comprising said means to support, and being spring-loaded to an upwardly extended position with said mandrel extending upwardly from a top end of said piston assembly.

19. The process as defined in claim 18 including inlet means to direct compressed air from a suitable source to bottom ends of said piston assembly to coact with said spring-loading to force said softened tip end into said tapered through cavity.

20. The process as defined in claim 11 wherein a minor tube entry portion of said heated die means through cavity is cylindrical and conforms generally with a diameter of the catheter tube, a major interior portion of the cavity defines a relatively gentle taper; and a relatively short top end portion thereof defines a substantially increased degree of taper.

21. The process as defined in claim 17 wherein said cam is configurated to define a minor dwell portion and a major high portion defining a plurality of outwardly extending lobes thereabout to transmit an up-down jogging movement to said heated die during the tube end taper formation.

22. The process as defined in claim 20 wherein a tip end of said meandrel seats against said increased taper portion adjacent to an inner opening defined thereby.

23. The process of forming a feathered tip on the tip zone of a tube of plastic material, said tip zone having a proximal and a distal portion, said process comprising the steps of:
positioning the tube in coaxial relation over a mandrel with the mandrel extending from the tip zone of the tube;
advancing a die over a portion of the tube and extending mandrel to a position with the die contacting the mandrel in annular relation;
applying heat to the tube at the distal zone and, simultaneously, supporting and cooling the proximal zone to avoid wrinkling of the tube; and
yieldingly supporting the mandrel while the heat is applied with the mandrel in sealing and heat exchanging relation with the die and with the die in heat exchanging relation with the tip.

24. A process of forming a feathered tip on the tip zone of a tip of plastic material, said tip zone having a proximal and a distal portion, said process comprising the steps of:

positioning the tube in coaxial relation over a mandrel with the mandrel extending from the tip zone of the tube;

advancing a die over a portion of the tube and extending the mandrel to a position with the die contacting the mandrel in annular relation, and depressing the mandrel relative to the tube and thereby forcing the distal zone to the inner extremity of a cavity within the die;

applying heat to the tube at the distal zone and, simultaneously supporting and cooling the proximal zone to avoid wrinkling of the tube; and yieldingly supporting the mandrel while the heat is applied with the mandrel in sealing and heat exchanging relation with the die and with the die in heat exchanging relation with the tip.

25. The process as set forth in claim 24 comprising the step of cyclically pulsing the mandrel and the die to release gas.

26. The process as in claim 25 comprising the step of yieldingly supporting the tube being provided with the feathered tip for axial movement of adjustment between the die and mandrel while the heat is being applied.

* * * * *